(12) United States Patent
Pflaum et al.

(10) Patent No.: US 6,264,364 B1
(45) Date of Patent: Jul. 24, 2001

(54) MEDICAL X-RAY SYSTEM SUITED FOR ANGIOGRAPHY

(75) Inventors: Michael Pflaum, Adelsdorf (DE); Ewald Popp, Taeby (SE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/377,779

(22) Filed: Aug. 20, 1999

(30) Foreign Application Priority Data

Aug. 31, 1998 (DE) .............................................. 198 39 620

(51) Int. Cl.⁷ ...................................................... H05G 1/02
(52) U.S. Cl. ................................................... 378/196; 378/4
(58) Field of Search .................................... 378/196, 197, 378/4, 193, 195, 198, 209

(56) References Cited

U.S. PATENT DOCUMENTS

| | | |
|---|---|---|
| 3,803,418 | * 4/1974 | Holstrom . |
| 4,298,801 | * 11/1981 | Heitman et al. . |
| 5,014,292 | * 5/1991 | Siczek et al. ..................... 378/196 |
| 5,479,470 | 12/1995 | Stenfors . |
| 5,822,814 | * 10/1998 | Van der Ende ....................... 5/601 |

FOREIGN PATENT DOCUMENTS 44 36 828   3/1996   (DE) .

\* cited by examiner

*Primary Examiner*—Robert H. Kim
*Assistant Examiner*—Pamela R. Hobden
(74) *Attorney, Agent, or Firm*—Schiff Hardin & Waite

(57) ABSTRACT

A medical x-ray system, such as an angiography system has an x-ray tube that emits and a radiation receiver, which are arranged at a C-arm, a stand supporting the C-arm, which has an arm that is rotatably mounted at one end around a stationary axis, and a holding device supporting the C-arm, which is rotatably mounted at the other end of the stand, and a patient table The stand is mounted via its arm at the ceiling and is mounted such that the rotational axis of the arm is arranged substantially in alignment with the center line of the patient table.

4 Claims, 2 Drawing Sheets

MEDICAL X-RAY SYSTEM SUITED FOR ANGIOGRAPHY

BACKGROUND OF THE INVENTION

1. Field of the Invention

The present invention is directed to a medical x-ray system of the type suitable for conducting procedures and examinations.

2. Description of the Prior Art

Medical systems are known which include the basic components of an x-ray tube that emits x-rays and a radiation receiver that are arranged at a C-arm, a stand that supports the C-arm, the stand having an arm that is rotatably mounted at one end so as to be rotatable around a stationary axis, and a holding device carrying the C-arm, which is rotatably mounted at the other end of the arm, and a patient table.

European Application 0 670 145, for example, discloses such a system. The mounting of the stand, including an isocentrically structured C-arm with an x-ray tube and radiation receiver enables a horizontal displacement of the isocenter along the patient table. The arm of the stand at which the C-arm holding device is arranged is rotatably mounted at a fastening component, which is rigidly mounted at the floor. This fastening component and the rotational axis around which the arm is rotatable are disposed such that the rotational axis lies outside of the center line of the examination table, i.e. the rotational axis is laterally offset relative to the central longitudinal axis of the table. Although the apparatus described in this reference enables a horizontal displacement of the isocenter, which is the intersection of an imaginary line between the x-ray source and the radiation receiver and the extension of the rotational axis of the holding component, such displacement is only possible on one side of the patient, i.e. the stand can only be displaced from the left side of the patient, for example, due to the laterally offset arrangement of the stand. A rotation of the stand at the other side is not possible. This is problematic because access to the patient from the side on which the stand is located, is of necessity only possible in limited fashion. The support at the floor is a further access impediment, since the fastening component that is arranged at the floor and the arm also proceeds near to the floor and thus can be in the way.

SUMMARY OF THE INVENTION

It is an object of the present invention to provide an x-ray system of the above-described general type which avoids the aforementioned problems.

This object is achieved in an x-ray system in accordance with the invention wherein the stand is mounted at the ceiling via its arm, and is mounted such that the rotational axis of the arm is arranged substantially in alignment with the center line of the patient table.

In the inventive arrangement support at the floor is forgone in favor of mounting at the ceiling, i.e. not only the fastening component but also the stand arm, in particular, are arranged near the ceiling and thus do not impede access to the patient table. Further, it is inventively provided that the rotational axis of the arm is arranged in alignment with the center line, i.e. the center of the patient table and is not laterally offset thereto as in the aforementioned prior art. This allows the stand, which can be moved in the manner of a scissors blade, can be moved not only from the right side of the patient table but also from the left side of the patient table. Thus, access is no longer limited to one side, as is the case in conventional systems. Depending on the needs of the moment, the C-arm including x-ray means can be selectively positioned on either side. Advantageously, the displacement no longer blocks the access to the patient. Further, the central arrangement of the inventive system with respect to the longitudinal axis of the table enables complete lateral transverse access to the patient, and this is true from both sides of the patient. Thus, the inventive arrangement provides the possibility of being able to arbitrarily cover each area of the patient from either side.

Relative to the patient table, the arm can be arranged at the ceiling such that the rotational axis lies in the area of an end of the table. It is also possible to dispose the rotational axis more in the middle area relative to the center line, i.e. so that the bearing point of the arm, which is at the ceiling, lies above the table.

In order to enable a simple movement and a movement that does not require any effort by attendants, motorized means can be inventively provided for automatic movement of the stand. In order to also enable manual handling as a backup or augmentation the motorized means can be inventively decoupled.

DESCRIPTION OF THE PREFERRED EMBODIMENTS

Figure 1:
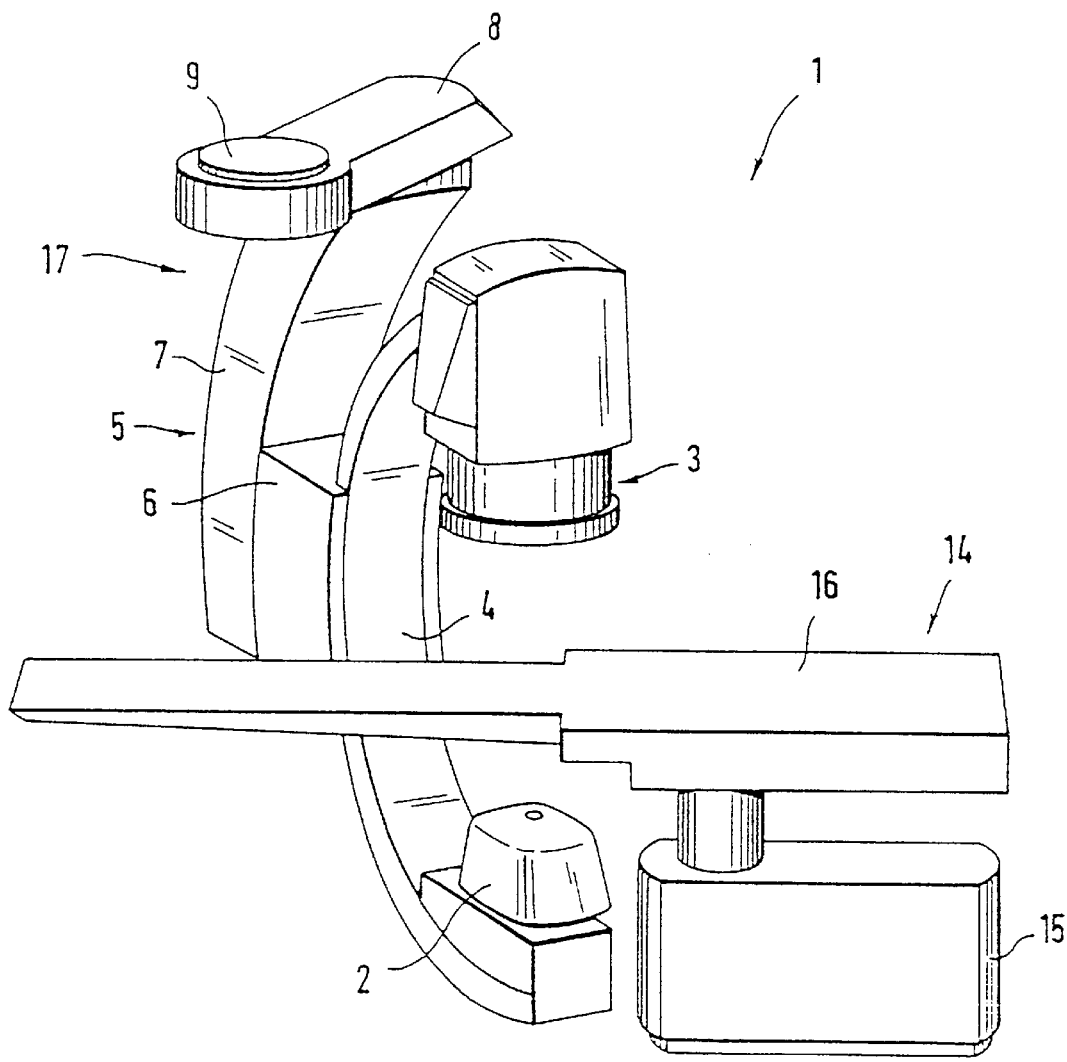
FIG. 1 is a respective schematic illustration of an inventive x-ray system.
Figure 2A:
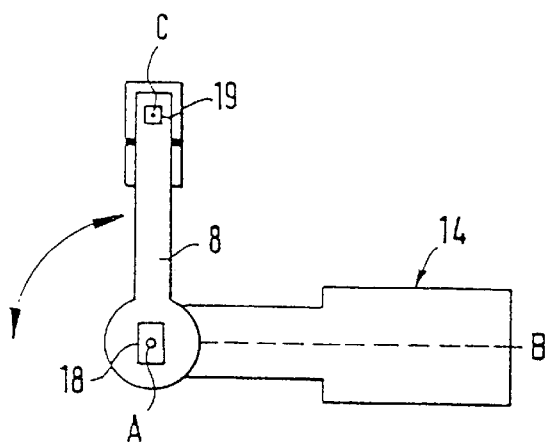
FIGS. 2a and 2b illustrate the movement of the stand and therewith to the x-ray arrangement on one side of the patient table in the system of FIG. 1.
Figure 2B:
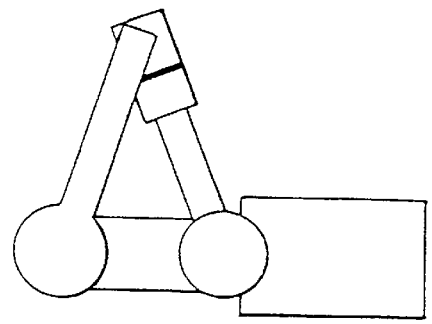
Figure 3A:
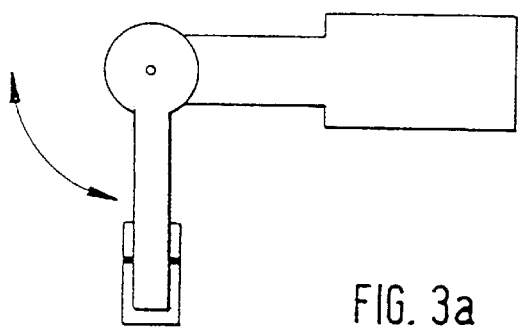
FIGS. 3a and 3b demonstrate the movement on the other side of the patient table in the system of FIG. 1.
Figure 3B:
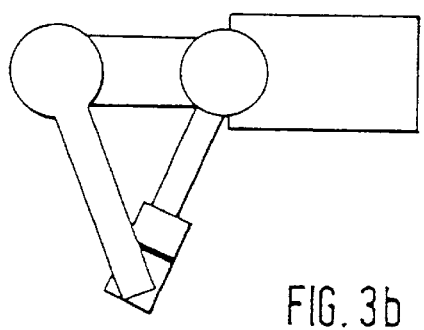

FIG. 1 shows an inventive x-ray system 1, having an x-ray tube 2 that emits x-rays and a radiation receiver 3 that is arranged opposite to the x-ray tube 2, which are mounted at a C-arm 4. The C-arm 4 in turn is arranged at a holding device 5 has a first part 6 at which the C-arm 4 is displaceably mounted, and a second part 7 at which the first part 6 is rotatably mounted. The holding device 5 itself is rotatably arranged at an arm 8 via the second part 7; the arm 8 being arranged at the ceiling via a fastening component 9, with respect to which it is also rotatably mounted. The system also includes a patient table 14 that is arranged at the floor via a table base 15. The patient table 14 has a table-top 16 that can be longitudinally and transversely displaced.

As is shown in FIGS. 2a through 4b, the stand, which is generally referenced 17, with the rotational axis A of the arm 8 is arranged at the ceiling such that the rotational axis A is an extension or is in alignment with, the center line B of the patient table 14 or the table-top, in the area of the table end in the given example. As shown in FIGS. 2a, 2b and 3a, 3b, this central arrangement enables selective displacement of the stand 17 including C-arm and x-ray components on the one table-top side, i.e. on the left side for example (FIGS. 2a, 2b) or on the other table-top side (on the right side, see FIGS. 3a, 3b). Depending on particular requirements, the C-arm can be positioned on either side, so that a patient access necessary from a specific side is always possible, since the components are movable to either side.

As can be further seen in the FIGS. 2a through 4b, it is possible without further difficulty to enable a horizontal movement parallel to the center line B, i.e. it is possible to move the isocenter along the center line B. This expediently ensues by means of corresponding motorized drives 18, 19, which can be belt drives or chain drives motorized toothed rack drives, parallelogram arms and similar drives. The motorized drive 18 serves the purpose of rotating the arm 8 around the rotational axis A, the drive 19 serves the purpose of rotating the holding device 5, or the second part 7, around the rotational axis C. The operation of these drives is controlled via a control unit that is not shown. These motorized drives 18, 19 allow movement in an arbitrary direction. The drives 18, 19 can also be decoupled from their drive trains in order to enable manual movement. The drive 18, 19 can also be motorized drives independently of each other that are electronically coupled via path pick-ups or angle pick-ups.

Figure 4A:
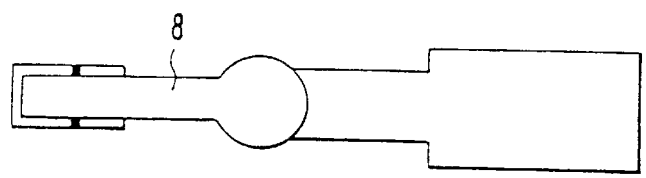
FIGS. 4a and 4b demonstrate the lateral movability for complete transverse access of the patient in the system of FIG. 1
Figure 4B:
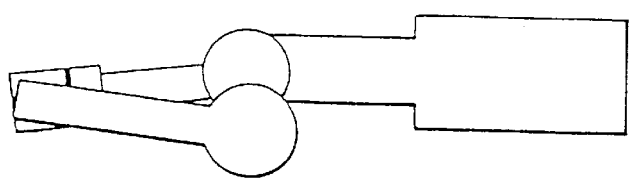

FIGS. 4a, 4b show the possibility of a purely lateral displacement, the C-arm including x-ray components being perpendicularly moved relative to the center line.

As shown in FIGS. 2a through 4b, the movement possibilities, which respectively proceed in selected directions, demonstrate that it is possible with the inventive support of the stand or arm at the ceiling and oriented toward the center line, to be able to cover any arbitrary area of the patient without being limited to a specific side of the table with respect to the movement of the C-arm. Therefore, the isocenter can be horizontally displaced in an arbitrary manner. Arbitrary patient access can be guaranteed without a component of the stand or C-arm constituting an impediment.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical x-ray system comprising:
   an x-ray tube which emits x-rays;
   a radiation detector on which x-rays from said x-ray tube are incident;
   a C-arm on which said x-ray tube and said radiation detector are mounted;
   a patient table adapted to receive a patient to be irradiated with said x-rays, said patient table having a central longitudinal axis; and
   a mounting arrangement for said C-arm, said mounting arrangement comprising an arm adapted to be rotationally mounted at a ceiling, a holding device which engages said C-arm and which is coupled with said arm for producing scissors blade-like relative movement between said arm and said holder, said holding device extending downwardly from said arm, and said arm being rotatable around a stationary rotational axis which intersects said central longitudinal axis of said patient table.

2. An x-ray system as claimed in claim 1 wherein said patient table has an end, and wherein said stationary rotational axis of said arm of said mounting arrangement intersects said central longitudinal axis of said patient table at said end.

3. An x-ray system as claimed in claim 1 further comprising a first motor for moving said arm and a second motor for moving said holding device.

4. An x-ray system as claimed in claim 3 further comprising means for decoupling said first motor from said arm and said second motor from said holding device for allowing manual movement of said arm and said holding device.

* * * * *